US005801279A

United States Patent [19]

Miura et al.

[11] Patent Number: 5,801,279
[45] Date of Patent: Sep. 1, 1998

[54] METHOD FOR REMOVING IODINE COMPOUNDS CONTAINED IN ORGANIC MEDIUM

[75] Inventors: Hiroyuki Miura; Masanobu Kayajima, both of Hyogo; Takashi Sato, Hiroshima, all of Japan

[73] Assignee: Daicel Chemical Industries, Ltd., Osaka, Japan

[21] Appl. No.: 835,486

[22] Filed: Apr. 8, 1997

[30] Foreign Application Priority Data

Apr. 26, 1996 [JP] Japan ................. 8-106520

[51] Int. Cl.$^6$ ................. C07C 51/42; C07C 53/08; C07C 51/573
[52] U.S. Cl. ................. 562/608; 562/607; 562/898
[58] Field of Search ................. 562/608, 607, 562/898

[56] References Cited

U.S. PATENT DOCUMENTS

| | | | |
|---|---|---|---|
| 4,615,806 | 10/1986 | Hilton | 210/690 |
| 5,139,981 | 8/1992 | Kurland | 502/11 |
| 5,220,058 | 6/1993 | Fish et al. | 562/608 |
| 5,227,524 | 7/1993 | Jones | 562/608 |

FOREIGN PATENT DOCUMENTS 0 482 787  4/1992  European Pat. Off. .

*Primary Examiner*—Gary Geist
*Assistant Examiner*—Rosalynd Keys
*Attorney, Agent, or Firm*—Flynn, Theil, Boutell & Tanis, P.C.

[57] ABSTRACT

An object of the present invention is to provide an operating method which can reduce the amount of silver or mercury dissolved in a solution after contact and can increase the usage of silver or mercury without installing new treating facilities in a process for removing iodine compounds contained in an organic medium, particularly acetic acid or a mixture of acetic acid or acetic anhydride, by contacting them with a cation exchange resin in which at least 1% of the active sites are converted to a silver form or a mercury form.

The operating method described above is characterized by carrying out the operation while elevating the temperatures in stages while contacting the organic medium, particularly acetic acid or a mixture of acetic acid and acetic anhydride, containing the iodine compounds with a cation exchange resin.

8 Claims, No Drawings

5,801,279

METHOD FOR REMOVING IODINE COMPOUNDS CONTAINED IN ORGANIC MEDIUM

FIELD OF THE INVENTION

The present invention relates to an operating method for removing iodine compounds from an organic medium by means of ion exchange resins, specifically to an operating method for removing iodine compounds contained in acetic acid or a mixture of acetic acid and acetic anhydride by contacting them with a cation exchange resin converted to a mercury form or a silver form.

DESCRIPTION OF THE RELATED ART

Various methods for removing iodine compounds from organic media are disclosed. Particularly, iodine compounds contained in acetic acid cannot completely be removed in some cases, even by distillation, and in the case where acetic acid is chemically changed to produce, for example, vinyl acetate, there is brought about the serious problem that contamination is caused by iodine compounds, which results in shortening of the life of a metal catalyst. Accordingly, many removal methods have been investigated.

Methods in which iodine compounds are removed by contacting them with strong acid cation exchange resins having active sites converted to a silver form or a mercury form are disclosed in a method for removing iodine compounds from acetic acid or a mixture of acetic acid and acetic anhydride. It is reported in, for example, JP-B 5-21031, that it is effective to use a macroreticular strong acid cation exchange resin in which at least 1% of the active sites have been converted to a silver form or a mercury form. It is described therein that the cation exchange resin can be used at temperatures falling in a range of from the solidifying point of an organic liquid up to the decomposition temperature of the resin, that is, 17° to 100° C. On the other hand, however, it is described that the temperatures are not important, and not only are descriptions on the temperatures not found in the examples, but also nothing is described about the operation of the running temperature.

It is disclosed in JP-A 4-282339 that a silver-containing meso-porous resin having a cross-linking degree of 6 to 10% can be used for removing iodine compounds. The typical temperature falls in a range of 20° to 120° C., and the temperature actually used in the examples is 43° C. The temperature used in JP-A 5-301839 falls in a range where the liquids are maintained, that is, 20° to 120° C., and the temperature actually used in the examples is 79° C.

It is reported in JP-B 7-14488 that a method using a cross-linked macroreticular resin obtained by combining silver ions with active sites thereof by ion exchange is effective. It is described that suitable operating temperatures fall in a range of from the solidifying point, 17° C., of acetic acid up to the boiling point, 118° C., of acetic acid and that the resin has a decomposition temperature of 150° C. or lower. Further, it is described that since the corrosion rate is increased at high temperatures, the removal should be carried out at as low a temperature as possible taking the desired removal rate into consideration. The temperatures are 20° C. in the examples and 40° C. in the comparative examples. However, the reaction rate is inferior at low temperatures and, therefore, the removal efficiency of iodine compounds and the usage of silver deteriorate.

Follow-up experiments for the examples described in these methods have been carried out by the present inventors to confirm the problems that, as a matter of fact, silver dissolves to some extent in acetic acid or a mixture of acetic acid and acetic anhydride obtained after contact with the ion exchange resins due to the nature of the ion exchange equilibrium of silver ions in an acid or because of the instability of the resins attributable to temperatures, to not only bring about the deterioration of the quality but also cause a deterioration in the silver usage. This is notable as the temperatures are elevated. Silver runs off markedly, for example, at 79° C., and therefore, such a temperature should not be employed.

It is reported in JP-B 5-21031 that it is convenient to put an ion exchange resin bed which has not yet converted to a silver form after an ion exchange resin bed which has been converted to a silver form.

However, there are problems that a large quantity of the ion exchange resins and a long resin-packed bed are required in order to recover a low concentration of silver and that the facilities cost a lot and a recovery cost is required, which raise the total cost.

Further, as described above, the reaction mechanism of iodine compounds with carried silver has not yet been analyzed, and the reaction rate and removal performance in the insides of macroreticular resins and meso-porous resins are not yet satisfactory.

SUMMARY OF THE INVENTION

An object of the present invention is to provide an operating method which can reduce the amount of silver or mercury dissolved in a solution after contact and can improve the usage of silver or mercury without installing new treatment facilities in a process for removing iodine compounds contained in an organic medium, particularly acetic acid or a mixture of acetic acid or acetic anhydride, by contacting them with a cation exchange resin in which at least 1% of the active sites are converted to a silver form or a mercury form.

The present inventors have kinetically investigated a mechanism for removing iodine compounds in a process for removing iodine compounds contained as impurities in an organic medium, particularly acetic acid and a mixture of acetic acid and acetic anhydride by contacting them with an ion exchange resin in which at least 1% of the active sites are converted to a silver form or a mercury form. As a result thereof, they have noticed that the diffusion resistance in the pores of the resin is dominant and found that the diffusion rate and the reaction rate can be raised by elevating the operating temperatures to increase notably the removal efficiency and life of the resin. Further, they have found that the problems of the run-off of silver or mercury due to an ion exchange equilibrium and the run-off of silver or mercury and sulfate radicals due to the deterioration of the resin are increased. The present inventors have found from these matters that the deterioration of the resin and the run-off of silver or mercury can be suppressed to the lowest level, and the removal efficiency, life of the resin and usage of silver or mercury can markedly be raised by contacting the organic medium containing iodine compounds with the ion exchange resin at relatively low temperatures during the beginning of the operation to maintain the deterioration of the resin and run-off amount of silver or mercury at low levels and then elevating the temperature in stages when an alkyl iodide such as hexyl iodide is about to be or has been detected in the vicinity of the exit of the resin bed, and thus the present invention has been completed. That is, the present invention relates to an operating method in which the amount of silver or mercury dissolved in a solution obtained after contact can easily be reduced, the iodine compounds can be most efficiently removed and the usage of silver and mercury can be improved by carrying out the operation while elevating the temperature in stages.

The invention is directed to a process for removing iodine compounds from an organic medium, which comprises the step of bringing the organic medium into contact with a cation exchange resin in which at least 1 percent of the active sites thereof have been changed to silver or mercury, while elevating the contacting temperature step by step or gradually in a continuous way.

It is preferable to elevate the temperature by 1 to 70 degree C., more preferably, by 2 to 25 degree C., in particular, by 3 to 15 degree C. The temperature may be elevated continuously at a low rate, for example, 1 to 70 degree C. per year, more preferably, by 2 to 25 degree C. per year, in particular, by 3 to 15 degree C. per year. It may be elevated step by step.

The product mixture of acetic acid may be taken out of a distillation column and cooled down to a given temperature before the treatment with a cation exchange resin. When the temperature of the ion exchange resin bed is higher than that of the product mixture, this may be heated to a given one.

The iodine-removing step can be conducted until the ion exchange resin has reached saturation (break through point).

DETAILED DESCRIPTION OF THE INVENTION

The present invention shall specifically be explained below.

The ion exchange resin used in the present invention is preferably a cation exchange resin comprising a sulfonated copolymer of styrene and divinylbenzene.

The method for converting the ion exchange resin to a silver form or a mercury form is not particularly important, and any silver salts can be used as long as they have a suitable solubility in water or a non-aqueous organic medium. Silver oxide, silver acetate and silver nitrate are typical examples thereof. The required amount of silver is more than the equivalent of the iodine compounds to be removed in terms of mole ratio.

An average pore diameter of the ion exchange resin is preferably 100 angstroms or more, more preferably 600 angstroms or more.

The organic medium containing the iodine compounds includes an organic acid, alcohol and ester. In particular, the operating method of the present invention is suited for the removal of iodine compounds contained in acetic acid or a mixture of acetic acid and acetic anhydride. More specifically, it is suited for the removal of iodine compounds contained in acetic acid or a mixture of acetic acid and acetic anhydride obtained by reacting at least one selected from methanol, methyl acetate and dimethyl ether with carbon monoxide or a mixture of carbon monoxide and hydrogen in the presence of a catalyst system containing a rhodium compound, methyl iodide and an alkaline metal iodide as a cocatalyst. The present invention shall not be restricted to the removal of halides contained in the organic medium and can be applied to the removal of halides contained in water or an aqueous solution.

The iodine compounds include alkyl iodides having a carbon number of up to about 10 such as hydrogen iodide, methyl iodide, ethyl iodide, propyl iodide, butyl iodide, pentyl iodide, hexyl iodide, heptyl iodide and octyl iodide, and a mixture thereof. The operating method of the present invention is effective as well for the removal of inorganic iodides such as lithium iodide and iodine ions. Further, it is effective for the removal of halogens other than iodine, for example, chlorine including alkyl chlorides having a carbon number of up to about 10, inorganic chlorides and chlorine ions. The amount thereof is about 0.1 to 1000 ppb in terms of concentration in a liquid.

In general, when ion exchange resins are industrially used, liquids to be treated are continuously passed through a packed bed in which the resins are filled. However, the resins may be used batchwise or by a fluidized bed method. When they are used in a continuous flow system, a flow rate and a bed volume per hour which reduces the influence exerted by a boundary diffusion resistance are generally employed, and the economically advantageous conditions may be employed according to the characteristics of the resins used and the kinds, characteristics and concentrations of the iodine compounds to be removed.

The lower limit of the temperature of using the ion exchange resins is 17° C., which is the solidifying point of acetic acid, and the upper limit thereof is 120° C., which is the heat resistant temperature of the resin. Temperatures exceeding 90° C. bring about the deterioration of the resin, which cannot be ignored, and therefore, a temperature falling in the range of 20° to 90° C. is preferably selected. In the method for elevating the temperature in stages, the operation is carried out preferably at a relatively low temperature of 17° to 35° C. at the beginning of the operation of using the resin for removing the iodine compounds during the time expended until the resin bed is used to its maximum, that is, saturation (arrive at the break through point), while maintaining the run-off amount of silver or mercury at a low level. Then, the temperature is elevated to the second stage, for example, about 45° C., to shorten the length of the adsorption band and the moving rate of the adsorption band. That is, the utilization is raised; the resin life, which is the time expended until saturation, is extended; and the usage is improved. The more the temperature is elevated, the more this effect is improved, but also, the more the run-off loss amount of silver or mercury increases as well. Accordingly, the temperature in the second stage is preferably elevated by about 10° C. At the temperature in the second stage, the resin bed is used for removing the iodine compounds while maintaining the run-off amount of silver or mercury at a low level until the resin bed is saturated (breakthrough point). Then, the temperature is elevated to the third stage, for example, about 55° C., to shorten the length of the adsorption band and the moving rate of the adsorption band to extend the resin life and increase its usage. Hereafter, the above procedures are repeated, whereby the deterioration of the resin and the run-off of silver or mercury can be minimized, and the efficiency of removing alkyl iodides, the resin life and the usage of silver or mercury can notably be improved.

In general, a stainless material is used in handling acetic acid and can be used at 120° C. without having any anxiety regarding corrosion.

These methods are not restricted to cases using the ion exchange resins and can be applied to cases using industrially usable carriers, for example, alumina, silica, silica alumina, zeolite and activated carbon carrying silver or mercury.

According to the present invention, the temperatures are elevated in stages to carry out the operation, whereby the deterioration of the resin and the run-off of silver or mercury can be minimized, and the efficiency of removing alkyl iodides, resin life and usage of silver or mercury can notably be improved.

EXAMPLES

The present invention shall more specifically be described below with reference to the examples, but the present invention shall not be restricted by these examples.

Iodine compounds contained in the organic media shown in Comparative Example 1 and Examples 1 and 2 were removed by the following method.

Acetic acid containing 15 to 20 ppb of hexyl iodide was continuously contacted with a packed bed of a strong acid cation exchange resin carried on active sites with silver and having a macroreticular structure while maintaining prescribed temperatures. Acetic acid after contacting was taken out of a sampling port attached to the column at a fixed interval to analyze the concentration of hexyl iodide by means of a gas chromatograph (ECD-GC) equipped with an electron capture type detector to confirm the removal state thereof and analyze the silver concentration by atomic absorption analysis. The ion exchange resin used was Amberlist 15 in which 41% of the active sites are converted to a silver form, manufactured by Rohm & Haas Co., Ltd. The column used had an inner diameter of 26 mm and a resin-packed height of 1600 mm. This column had sampling ports disposed at four spots.

Comparative Example 1

Concentrations of silver contained in an effluent in the beginning of the operation and the stable operation were determined, wherein acetic acid containing the iodine compounds was contacted with a packed bed of the ion exchange resin converted to a silver form at a flow rate of 12.8 bed volume per hour (1 bed volume is 616 ml). The experiments were carried out independently at operating temperatures of 28° C., 54° C. and 70° C., respectively. The concentrations of silver contained in the effluents are shown in Tables 1 to 3. Hexyl iodide was not detected at the exit of the resin-packed bed.

In the case of 54° C., which is higher by 26° C. than 28° C., the silver dissolved in acetic acid after contact about four times as much an amount as in the case of 28° C. In the case of 70° C., which is higher by 42° C. than 28° C., the silver dissolved in acetic acid after contact about eleven times as much an amount as in the case of 28° C. That is, it can be found that the higher the operating temperature is, the greater the loss of silver.

TABLE 1

Concentration of silver contained in effluent (operation temperature: 28° C.)

| | Elapsed Time | Concentration of Silver (ppb) |
| --- | --- | --- |
| Beginning of operation | 816 hrs | 12 |
| Stable operation | 3179 hrs | 1.1 |

TABLE 2

Concentration of silver contained in effluent (operation temperature: 54° C.)

| | Elapsed Time | Concentration of Silver (ppb) |
| --- | --- | --- |
| Beginning of operation | 620 hrs | 43 |
| Stable operation | 1652 hrs | 14 |

TABLE 3

Concentration of silver contained in effluent (operation temperature: 70° C.)

| Elapsed Time | Concentration of Silver (ppb) |
| --- | --- |
| 1206 hours | 130 |

Example 1

The stable operation was carried out while contacting acetic acid containing iodine compounds with the ion exchange resin converted to a silver form at a temperature of 33° C. and a flow rate of 7.2 bed volume per hour, and the temperature was then elevated to 43° C. The silver concentrations determined during the operation are shown below.

TABLE 4

Concentrations of silver and sulfate radical contained in effluent (temperature was varied during continuous operation)

| | Elapsed Time | Concentration of silver | Concentration of sulfate radical |
| --- | --- | --- | --- |
| Beginning of operation (33° C.) | 24 hrs | 24 ppb | 130 ppb |
| | 187 hrs | 2.7 ppb | 2 ppb |
| Stable operation (33° C.) | 5683 hrs | 1.8 ppb | 1 ppb |
| After elevating temperature (43° C.) | 5803 hrs (total) (time) | 2.3 ppb | 4 ppb |

A marked run-off of silver was not observed even when the temperature was elevated at an intermediate stage of the operation.

Further, the usage of silver carried on the ion exchange resin was investigated based on the change in concentration of hexyl iodide in the packed bed with the lapse of time. As a result thereof, it has been found that an increase in the temperature by 10° C. from 33° C. to 43° C. shortens the length of the absorption band by 0.83 time and the moving rate of the absorption band by 0.69 time, that is, it raises the usage to extend the resin life by about 1.4 times.

Thus, the resin bed was used for the removal of hexyl iodide at a low temperature of 33° C. during the period until the resin bed was close to saturation at the beginning of the operation, and then the temperature was elevated to 43° C., whereby the run-off loss amount of silver was controlled to a low level, and the resin life extended.

Example 2

The stable operation was carried out while contacting acetic acid containing iodine compounds with the ion exchange resin converted to a silver form at a temperature of 28° C. and a flow rate of 12.8 bed volumes per hour, and the temperature was then elevated to 54° C. The silver concentrations determined during the operation are shown below.

TABLE 5

Concentrations of silver and sulfate radical contained in effluent (temperature was varied during continuous operation)

|  | Elapsed Time | Concentration of silver | Concentration of sulfate radical |
|---|---|---|---|
| Beginning of operation (28° C.) | 816 hrs | 12 ppb | 8 ppb |
| Stable operation (28° C.) | 3179 hrs | 1.1 ppb | 1 ppb |
|  | 7485 hrs | 2.0 ppb | 1 ppb |
| After elevating temperature (54° C.) | 8807 hrs (total time) | 3.7 ppb | 1 ppb |

A marked run-off of silver was not observed even when the temperature was elevated at an intermediate stage of the operation.

Further, the usage of silver carried on the ion exchange resin was investigated based on the change in concentration of hexyl iodide in the packed bed with a lapse of time. As a result thereof, it has been found that a rise in the temperature to 54° C. extended the resin life by 2.1 times as compared with that in the case of 28° C. Further, a subsequent rise to 70° C. extended the resin life by 3.7 times as compared with that in the case of 28° C.

It has been found from the results summarized in Tables 1 to 3 that the earlier the stage of the operation is and the higher the temperature is, the more the run-off amount of silver. Accordingly, the marked run off of silver can be reduced and the usage of silver carried on the ion exchange resin can be raised by carrying out an operating method in which the operation is carried out at relatively low temperatures in the beginning and the temperature is elevated when the contact of acetic acid containing the iodine compounds with the ion exchange resin converted to a silver form is stabilized.

We claim:

1. In a process for removing iodine compounds from an organic medium in which the organic medium containing the iodine compounds is brought into contact with a cation exchange resin having at least 1% of its active sites converted to a silver or mercury form to remove the iodine compounds from the organic medium, the improvement comprising the steps of: initially contacting the cation exchange resin with the organic medium containing the iodine compounds at an initial temperature and incrementally increasing the temperature in an amount of from 2° to 25° C. during the contacting of the cation exchange resin with the organic medium containing the iodine compounds to remove the iodine compounds therefrom.

2. The process as claimed in claim 1, wherein the organic medium is acetic acid or a mixture of acetic acid and acetic anhydride.

3. The process as claimed in claim 1, wherein the iodine compounds are alkyl iodides.

4. The process as claimed in claim 2, wherein the acetic acid or mixture of acetic acid and acetic anhydride is contacted with the cation exchange resin at temperatures of 17° to 120° C. and a flow rate of 0.5 to 40 bed volume per hour.

5. The process as claimed in claim 4, wherein the acetic acid or mixture of acetic acid and acetic anhydride is contacted with the cation exchange resin at an initial temperature of from 17° to 35° C.

6. The process as claimed in claim 1, wherein the iodine compound is at least one member selected from the group consisting of methyl iodide and hexyl iodide.

7. The process of claim 1, wherein the temperature is increased incrementally in an amount of from 3° to 15° C.

8. The process of claim 1, wherein the temperature is increased incrementally after the cation exchange resin reaches saturation at the initial temperature.

* * * * *